United States Patent
Scorsin et al.

(10) Patent No.: US 10,779,934 B2
(45) Date of Patent: Sep. 22, 2020

(54) PROSTHETIC MONOLEAFLET VALVE AND DELIVERY DEVICE

(71) Applicant: Epygon, Paris (FR)

(72) Inventors: Marcio Scorsin, Curitiba (BR); Enrico Pasquino, Savigny (CH); Sergio Casalegno, San Mauro Torinese (IT)

(73) Assignee: Epygon, Paris (FR)

( * ) Notice: Subject to any disclaimer, the term of this patent is extended or adjusted under 35 U.S.C. 154(b) by 202 days.

(21) Appl. No.: 15/122,221

(22) PCT Filed: Mar. 9, 2015

(86) PCT No.: PCT/EP2015/054861
§ 371 (c)(1),
(2) Date: Aug. 29, 2016

(87) PCT Pub. No.: WO2015/135883
PCT Pub. Date: Sep. 17, 2015

(65) Prior Publication Data
US 2016/0367359 A1    Dec. 22, 2016

(30) Foreign Application Priority Data
Mar. 11, 2014 (EP) .................................. 14305354

(51) Int. Cl.
*A61F 2/24* (2006.01)
*A61F 2/95* (2013.01)

(52) U.S. Cl.
CPC .......... *A61F 2/2418* (2013.01); *A61F 2/2412* (2013.01); *A61F 2/95* (2013.01);
(Continued)

(58) Field of Classification Search
CPC .................................................. A61F 2/2412
See application file for complete search history.

(56) References Cited

U.S. PATENT DOCUMENTS

| | | | | |
|---|---|---|---|---|
| 4,759,758 A | * | 7/1988 | Gabbay | A61F 2/2412 623/2.13 |
| 2003/0060875 A1 | * | 3/2003 | Wittens | A61F 2/2418 623/1.23 |

(Continued)

FOREIGN PATENT DOCUMENTS

| | | |
|---|---|---|
| JP | 2013-526388 | 6/2013 |
| WO | WO9829057 | 7/1998 |

(Continued)

OTHER PUBLICATIONS

International Search Report (ISR) dated Jun. 12, 2015 of parent case PCT/EP2015/054861.

(Continued)

*Primary Examiner* — Rebecca S Preston
(74) *Attorney, Agent, or Firm* — Andre Roland S.A.; Nikolaus Schibli

(57) ABSTRACT

A prosthetic valve, preferably an expandable prosthetic valve, having a valve component (3), preferably a mitral valve component, made of a single functional leaflet (6) wherein the prosthetic valve (1) comprises at least two tissue supports (4', 4",4''',4'''') attachable to an inner surface (5) of a stent component (2), wherein at least one tissue support (4', 4",4''',4'''') comprises at least one attachment area (7', 7"), at least a section of the attachment area extending essentially inwardly from the inner surface (5), wherein said leaflet (6) is attached to at least one tissue support (4', 4",4''',4'''') at the section of said attachment area(s) (7', 7") such that the leaflet (6) is arranged between said attachment area(s) (7',7") or integrally formed with one tissue support (4',4",4''',4'''') and attached to the second tissue support (4',4",4''',4'''') at the section of the attachment area(s) (7',7").

22 Claims, 7 Drawing Sheets

Figure 1:
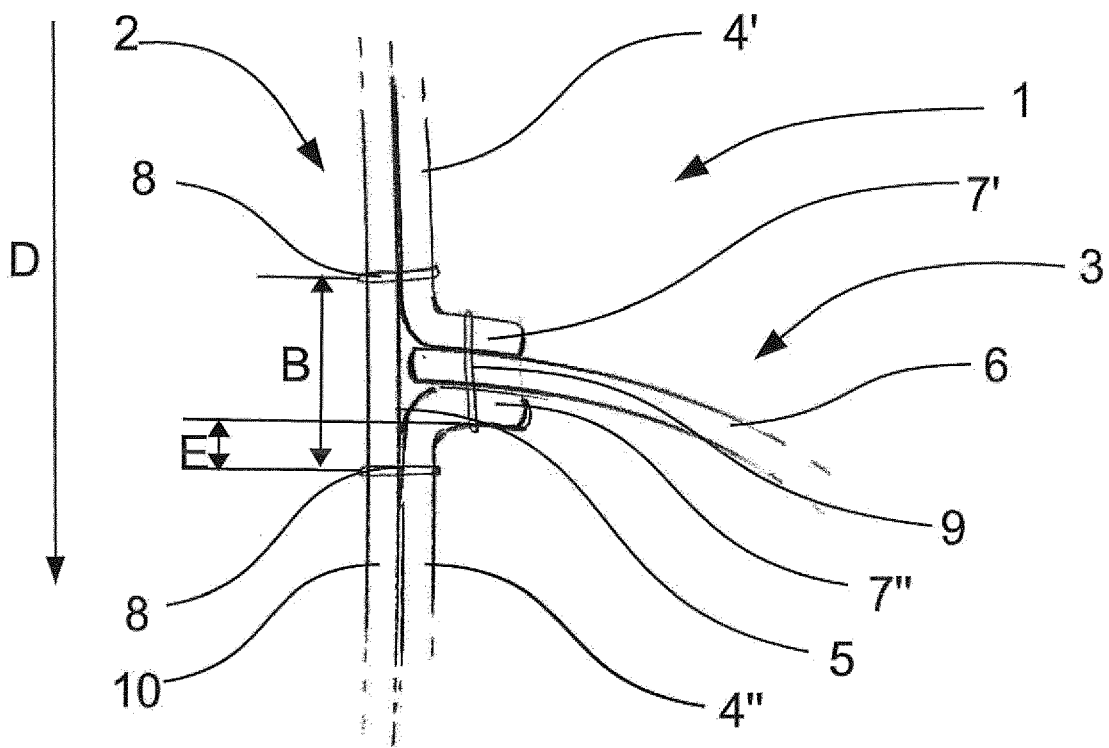

(52) U.S. Cl.
CPC ..... *A61F 2/2427* (2013.01); *A61F 2220/0075* (2013.01); *A61F 2230/0034* (2013.01); *A61F 2250/0037* (2013.01); *A61F 2250/0039* (2013.01); *A61F 2250/0069* (2013.01)

(56) References Cited

U.S. PATENT DOCUMENTS

| | | |
|---|---|---|
| 2003/0199975 A1 | 10/2003 | Gabbay |
| 2006/0259135 A1 | 11/2006 | Navia et al. |
| 2007/0288086 A1 | 12/2007 | Kalmann et al. |
| 2009/0105813 A1* | 4/2009 | Chambers ............. A61F 2/2412 623/2.12 |
| 2009/0132037 A1 | 5/2009 | Hoffman et al. |
| 2009/0254176 A1 | 10/2009 | Butera |
| 2009/0281618 A1 | 11/2009 | Hill et al. |
| 2010/0023120 A1 | 1/2010 | Holecek et al. |
| 2010/0114307 A1 | 5/2010 | Agnew et al. |
| 2010/0185277 A1 | 7/2010 | Braido et al. |
| 2011/0295363 A1 | 12/2011 | Girard et al. |
| 2011/0319989 A1 | 12/2011 | Lane et al. |
| 2012/0197388 A1 | 8/2012 | Khairkhahan et al. |
| 2013/0023984 A1 | 1/2013 | Conklin |
| 2017/0079789 A1 | 3/2017 | Braido et al. |
| 2018/0008405 A1 | 1/2018 | Girard et al. |

FOREIGN PATENT DOCUMENTS

| | | |
|---|---|---|
| WO | WO2004082527 | 9/2004 |
| WO | WO2006132948 | 12/2006 |
| WO | WO2009079475 | 6/2009 |
| WO | WO2012106011 | 8/2012 |
| WO | WO2013/160439 A1 | 10/2013 |

OTHER PUBLICATIONS

Written Opinion of the International Search Authority (WOSA) dated Jun. 12, 2015 of parent case PCT/EP2015/054861.
First Office Action dated Jan. 31, 2018, issued in the European Patent Application No. 15713398.4.
First Office Action dated Jul. 25, 2017, issued in Chinese Patent Application No. 201580013469.1.
Final Office Action dated Jun. 4, 2018 of a related case with the U.S. Appl. No. 14/396,254.
Non-final Office Action dated May 18, 2018 of a related case with the U.S. Appl. No. 15/122,642.
Japanese Patent Application 2016-556711 Office Action dated Nov. 20, 2018 with English translation.
Japanese Office Action for counterpart application 2016-556711 dated Nov. 20, 2018 with English translation.
Green et al., "Restricted posterior leaflet motion after mitral ring annuloplasty." The Annals of thoracic surgery 68, No. 6 (1999): 2100-2106.
Perier et al., "Toward a new paradigm for the reconstruction of posterior leaflet prolapse: midterm results of the "respect rather than resect" approach." The Annals of thoracic surgery 86, No. 3 (2008): 718-725.
Klabunde, "Cardiovascular Physiology Concepts," 2nd Edition, Publisher Wolters Kluwer, Lippincott Williams & Wilkins, ISBN 978-1-4511-1384-6, 2005, pp. 93-105.
Klingensmith et al., "The Washington Manual of Surgery," Washington University School of Medicine, 5th Edition, 2008, Publisher Lippencott Williams & Wilkins, ISBN 978-0-7817-7447-5, pp. 512 Table 30-1.
Schwarz, Franz, et al. "The effect of aortic valve replacement on survival." Circulation 66, No. 5 (1982): 1105-1110.

\* cited by examiner

Fig.6
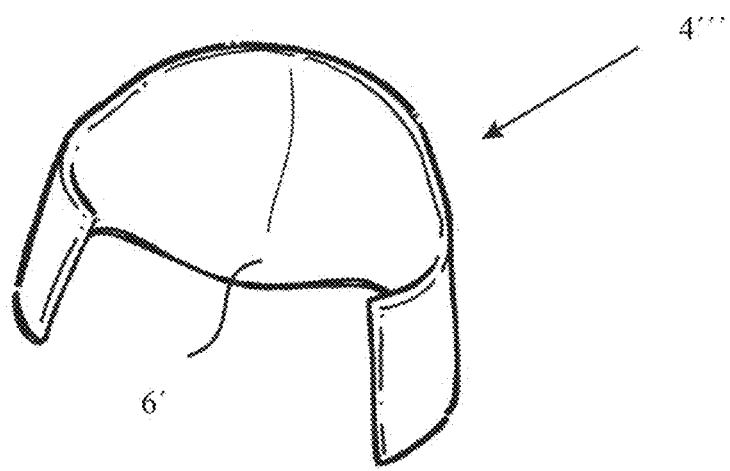
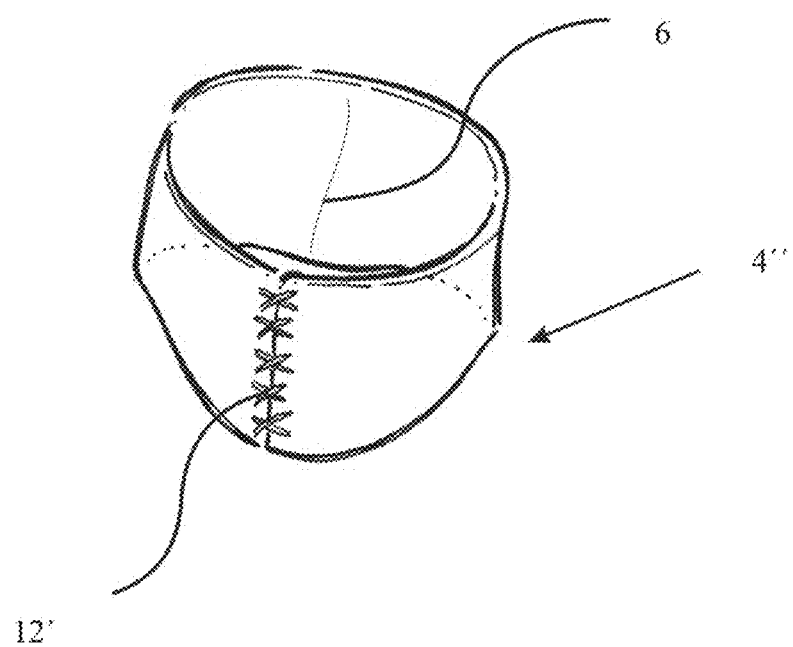
Fig.7

Fig.9
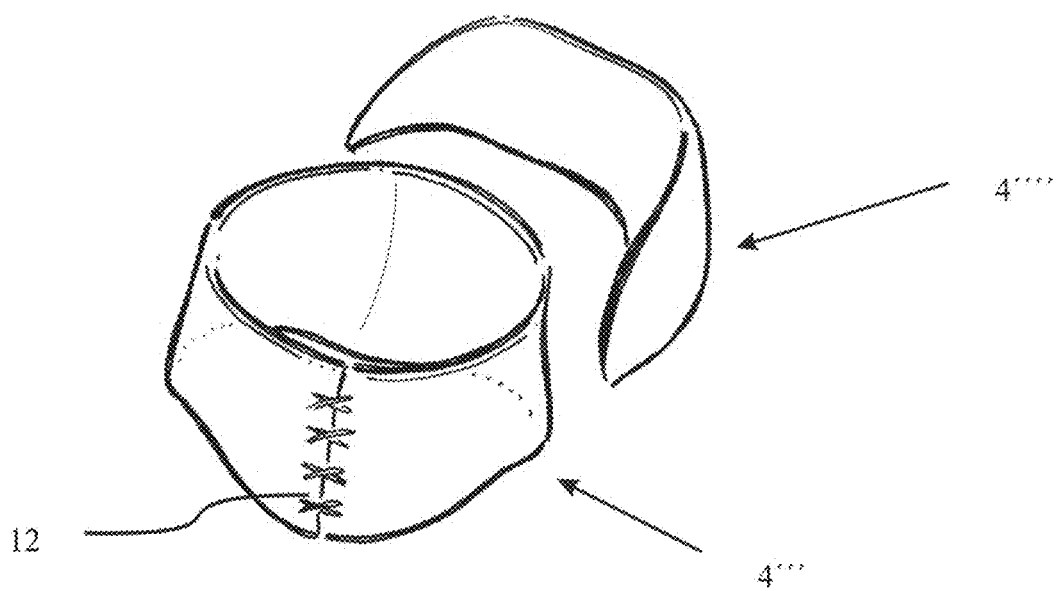
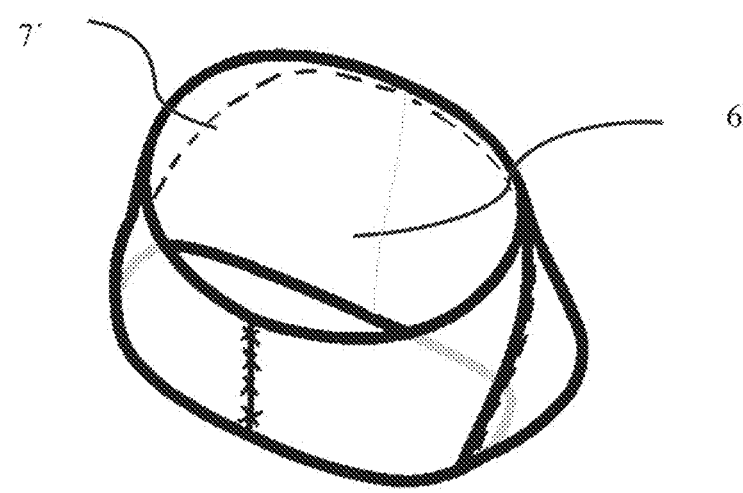
Fig.10

PROSTHETIC MONOLEAFLET VALVE AND DELIVERY DEVICE

CROSS REFERENCE TO RELATED APPLICATIONS

The present application is a United States national stage application of International patent application PCT/EP2015/054861 filed on Mar. 9, 2015 that designates the United States, and claims foreign priority to European patent application EP 14305354.4 filed on Mar. 11, 2014, the contents of these two documents being herewith incorporated by reference in their entirety.

The invention is directed to prosthetic valves and delivery devices for prosthetic valves. It more precisely relates to stent-valves wherein the valve component is made of a single functional leaflet.

The replacement of cardiac valves with prostheses is a complex operation. The replacement is often carried out by an open heart surgery. Such an operation requires the opening of the chest, as well as the arrest of the patient's heart. During the last years, minimally invasive systems have been established to percutaneously deliver a stent prosthesis by catheter.

Stents to be delivered by catheter have to be crimped in order to be mounted on or into the catheter. Upon arriving at an implantation site, the stent is released and expands either through self-expanding or with aid of auxiliary means such as balloons or wires.

A critical aspect of a functional expandable stent-valve is an attachment of valve leaflets to the stent. The attachment of the valve leaflets is often achieved with stitches at a commissural level of the prosthesis. Usually the leaflets are attached vertical and parallel to a longitudinal axis of the stent. Therewith, crimping of the stent can be facilitated. However, stress generated during opening and closing of the leaflets are mainly occurring at the stitches. These unevenly distributed stress may reduce the long-term durability of stent-valves. Furthermore, especially in asymmetric stents and/or stents with multiple leaflets, such an anchoring is problematic as the stitches might interfere with each other.

US 2013/0023984 suggests providing a stent with elongated projections at an outflow end. Leaflet tabs from each of two adjacent leaflets are extending through one common elongated projection. The passed through leaflet tabs are sutured together around a small component such as a pin. Therewith, the leaflets are attached to the stent. The sutures are arranged outside the stent to reduce stress.

However, the leaflets are bending over an edge of the projections during opening and closing. This results in high stress occurring on the leaflets adjacent to these edges of the projections. The stress reduces the long term durability of the leaflets and hence the stent-valve.

WO 2009/079475 proposes a solution with a two-part foldable stent-frame. The frame has an "upper part" and a "lower part" wherein each part is shaped with rounded arc portions to support leaflets. The leaflets are sandwiched between the upper and lower arc portions. A cloth is sewn to the leaflets. The leaflets comprising the cloth are then sandwiched between the two arcs. Afterwards, the cloth is wrapped over the arcs and sewn together to attach the leaflets to the frame.

However, the leaflets are bending over edges of the arc portions during opening and closing. This results in high stress occurring at the leaflets adjacent to an inner side of arcs. The stress reduces the long term durability of the leaflets and hence the stent-valve.

Hence, there is a need for prosthetic valves which avoid the disadvantage of the known state of the art. In particular, there is a need for prosthetic valves comprising valve leaflets which are attached to a stent or surgically to an annulus such that the stress is evenly distributed along parts of the leaflet and ensure long time durability of the leaflets The attachment should work for different stent-valves, e.g. symmetric or asymmetric stent valves, self-expandable and balloon expandable stent-valves, mono or multiple leaflet valves. The attachment should also work if directly attached to the annulus of a heart valve, i.e., without a stent component.

Herein, the invention is mainly described for a stent-valve comprising a mono leaflet valve for mitral valve replacement. The device is also suitable for direct implantation without a stent-component, e.g., by stitching the parts to the annulus.

The present invention provides a prosthetic valve, preferably an expandable prosthetic valve, having a valve component, preferably a mitral valve component, made of a single functional leaflet wherein the prosthetic valve comprises at least two tissue supports attachable to an inner surface of a stent component. The valve component comprises one leaflet, and wherein at least one tissue support comprises at least one attachment area. At least a section of the attachment area extends essentially inwardly from the inner surface. The leaflet is attached to the at least one tissue support at the section of said attachment area(s) such that the leaflet is arranged between said attachment area(s) or integrally formed with one tissue support and attached to the second tissue support at the section of the attachment area(s).

At least two tissue supports in the context of this application means that there are at least two sections. At least two tissue supports does include also two integrally formed sections (e.g. a section covering an inner surface of an inflow end of the stent and attached to second section covering an inner surface of an outflow end of the stent, connected sections), as well as separated, not connected sections.

The tissue support may extend along the entire circumference or only along parts of the circumference of the stent or the annulus. The attachment area may circumferentially extend along the complete tissue support or only along parts of the tissue support.

Preferably, the prosthetic valve further comprises a stent component. The at least two tissue supports are attached to an inner surface of the stent component and at least partly cover the inner surface of the stent component.

The tissue supports may be arranged such that the entire length of the stent is covered with tissue support or such that only parts of the length of the stent are covered with tissue support.

The leaflet is not directly and fixedly attached to the valvular stent but indirectly via one or more tissue supports. The attachment of the functional leaflet as well as the whole functional leaflet itself is completely inside the stent. Therefore, the leaflet is not bending over any struts or the like, e.g., during systo-diastolic opening. Therewith, the stress occurring along such bending lines are avoided.

The at least one leaflet is preferably elastic and the sutures preferably arranged at minimum distance 1 mm, preferably in the range of 1 mm to 5 mm, from the attachment area such that that the leaflet elastically absorbs chain shock during systo-diastolic leaflet opening and closure.

In an embodiment according to the present invention, the tissue supports as well as the leaflet preferably are elastic. With elastic components, the arrangement of at least two support tissues and the attached leaflet is elastic.

During cycles of leaflet opening and closing, pressures act on the leaflets. These pressures result in net forces on the leaflet mainly in upstream or downstream direction. With an elastic arrangement, the net forces, i.e. chain shocks can be elastically absorbed and cushioned. With the elastic absorption the leaflets and therefore the stent-valve have a longer lifetime of.

Alternatively, the tissue supports and/or the leaflet is not elastic or only slightly elastic. There is still an elastic chain shock absorption if at least one of the different parts is elastic.

The attachment of a leaflet, preferably a pericardium leaflet to tissue support is much more elastic than the attachment of a leaflet directly to a stent. The elasticity is about the same as the elasticity of the material alone, e.g. pericardium.

It is also possible to use other biologic or synthetic materials for leaflets and/or support tissues. The parts may also be of different material, e.g. one synthetic one biologic.

A suture to attach the tissue support is preferably running all along the stent. The suture is preferably arranged at a distance in the range of 1 mm to 5 mm, to the attachment area. Such a distance ensures the elastic absorption.

Preferably, the at least one leaflet is elastic and the sutures are arranged at a minimum distance of 2 mm from the attachment area such that all stress generated by the leaflet all along an insertion line to the tissue supports are evenly distributed to the stent surface.

The leaflet may be sandwiched between at least two tissue supports and separately formed from these at least two tissue supports. In case of more than one leaflet, the leaflets may all be circumferentially attached to the same tissue supports. Alternatively, the leaflets are attached to multiple separate support tissues arranged one besides the other in a circumferential direction.

Such an anchoring results a symmetric arrangement with an attachment area on both sides of the leaflet. The construction results in an optimal elastic shock absorption during systo-diastolic leaflet opening as both sides absorb the chain shock substantially identical.

The at least two tissue supports may be integrally formed and folded twice such that a five layer tissue results of which the middle one is the functional leaflet.

Preferably, the at least two tissue supports are, however, separated. The at least two tissue supports and the leaflet arrangement then results in a three layer tissue of which the middle one is the functional leaflet.

The arrangement with separate leaflets needs less material and is therefore more cost-efficient. Furthermore, the arrangement results in a relatively thin overlapping area of the tissue supports and the functional leaflet. The thin area interferes only slightly with medium passing through the stent allowing a less turbulent flow-through as compared to thicker areas.

The inner surface of the stent-component between neighbouring sections of the attachment areas attached to the leaflet is possibly not covered with tissue support. Therefore, with the at least two tissue supports separated, the inner surface of the stent component between the sections of the at least two tissue supports attached to the leaflet is not covered with another tissue support. Because of the functional leaflet, the not covered inner surface is not in direct contact with medium passing through the stent. Therefore, there is no mandatory requirement of an additional coverage of this area. By not covering the area, the construction can be kept simpler and more cost-efficient, as there is less tissue support needed.

Edge areas of the tissue support without an attached leaflet, are preferably overlapping. Therefore, the inner surface of the stent between the tissue support areas not attached to a leaflet is covered with tissue support(s).

In an alternative embodiment, the functional leaflet is integrally formed with one tissue support. "Integrally formed" in the context of this application means that the two parts are formed as one piece. The integrally formed leaflet is attached to the attachment area of the at least one further tissue support. This attachment results in a two layer tissue, one of which is the functional leaflet.

Such a two layer tissue arrangement is simple and relatively thin. The integral arrangement of one tissue support and the leaflet is very stable as the leaflet is only attached to one tissue support.

The leaflet may be integrally formed with the tissue support positioned at an inflow end of the stent-valve.

Alternatively, the leaflet may be integrally formed with the tissue support positioned at an outflow end of the stent-valve.

In another preferred embodiment, the functional leaflet is integrally formed with one tissue support in a way as to form a tubular body that, for instance, is made of pericardium.

The tubular body has a posterior part that is adapted to be fixed to the stent component and an anterior part that forms the functional leaflet. The other tissue support is attached to the anterior part of the tubular body (i.e. to the functional leaflet).

Advantageously the tubular made is obtained from a planar piece of tissue with opposite ends being sutured. The suture is preferably located on the tubular body posterior part.

The piece of tissue may have a substantially rectangular shape. Preferably, the rectangle width varies along one side of its length, in a way as to show a larger width in the middle of the rectangle.

Preferably, the leaflet in the different embodiments described herein is attached to the attachment area(s) with sutures.

The sutures are preferably non absorbable, biocompatible sutures, such as e.g. polyester (twisted or braided), monofilaments of polypropylene or Gore-tex threads. Further possible are silk threads or thin metal wires. The leaflet might be attached to the attachment areas using a sewing machine.

Alternatively, the leaflet may be attached with glue.

The shape of the attachment, i.e., sutures is not dependent on the stent component, as the leaflet is not directly attached to the stent, but to the tissue supports. The suture have preferably a shape of linear interrupted stitches or rhomboid stitches. The distance between the stitches is preferably as short as possible. The distance may range from 1.0 mm to 1.5 mm, but preferably not more than 2 mm.

Sutures have been shown to provide a stable and secure attachment for leaflets and the like. Alternatively the leaflet is attacked differently, e.g. with clamps or staples.

Preferably the at least two support tissues are attached to the inner surface of the stent-component with sutures.

The support tissues are preferably stitched to the stent through simple interrupted stitches basically following the vertical axis of the stent. The distance between the stitches is preferably 1.0 mm to 1.5 mm.

Sutures have been shown to provide a stable and secure attachment also for tissue supports, stent skirts, or the like to stents. Various shapes of stitches can be considered, e.g. linear or rhomboid shapes. Alternatively, the tissue supports are attached differently, e.g. with clamps, staples or glue.

The leaflet and/or the tissue supports are preferably substantially made of pericardium.

Substantially made of pericardium in the context of this application means that the main constituent is of pericardium but other substances may be present in smaller amounts. Pericardium is known to provide long-term stability. Further, pericardium has been shown to have a good biocompatibility.

Alternatively, other biocompatible materials may be used, e.g., biocompatible plastics or native animal valve leaflets.

The stent-valve is preferably self expandable. The stent-valve expands after release from a catheter to an expanded configuration without any auxiliary means. Typically, the self expanding stent-valve is formed out of a memory-shape material such as Nitinol. With a self expanding stent-valve no further means, except for the catheter, have to be introduced into the body for the process of expansion. There is less risk of complication without such means.

Alternatively, the stent-valve is not self expandable but expandable with the aid of auxiliary means such as a balloon or wires.

Preferably, the attachment area has a length of 2 to 10 mm. The attachment area has to be sufficiently large to allow the attachment of the leaflet in a way that the leaflet is retained in place without dislodgement.

Another aspect of the invention is a delivery device comprising a stent-valve according to the invention.

Further aspects of the invention are described relating to the figures. The figures show schematically:

FIG. 1: A longitudinal section through a stent valve

Figure 2:
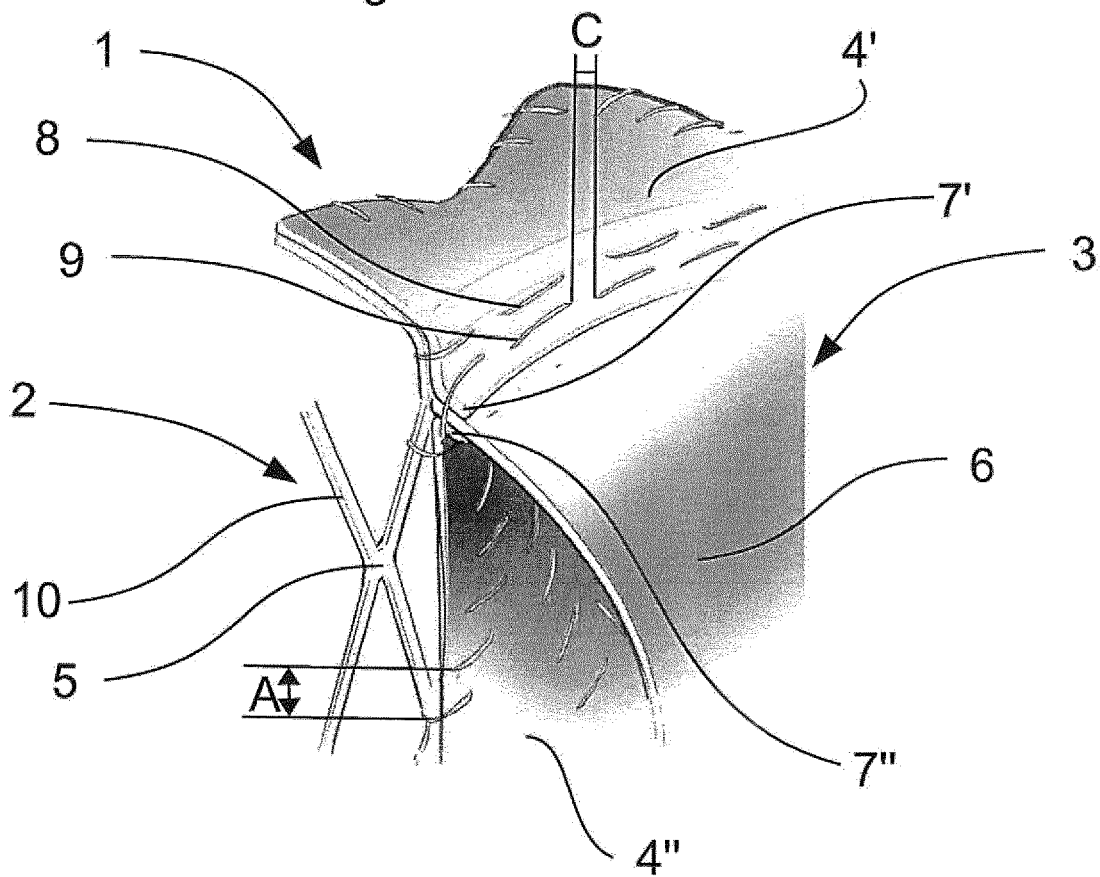

FIG. 2: An inside view of a stent-valve according to the invention

Figure 3:
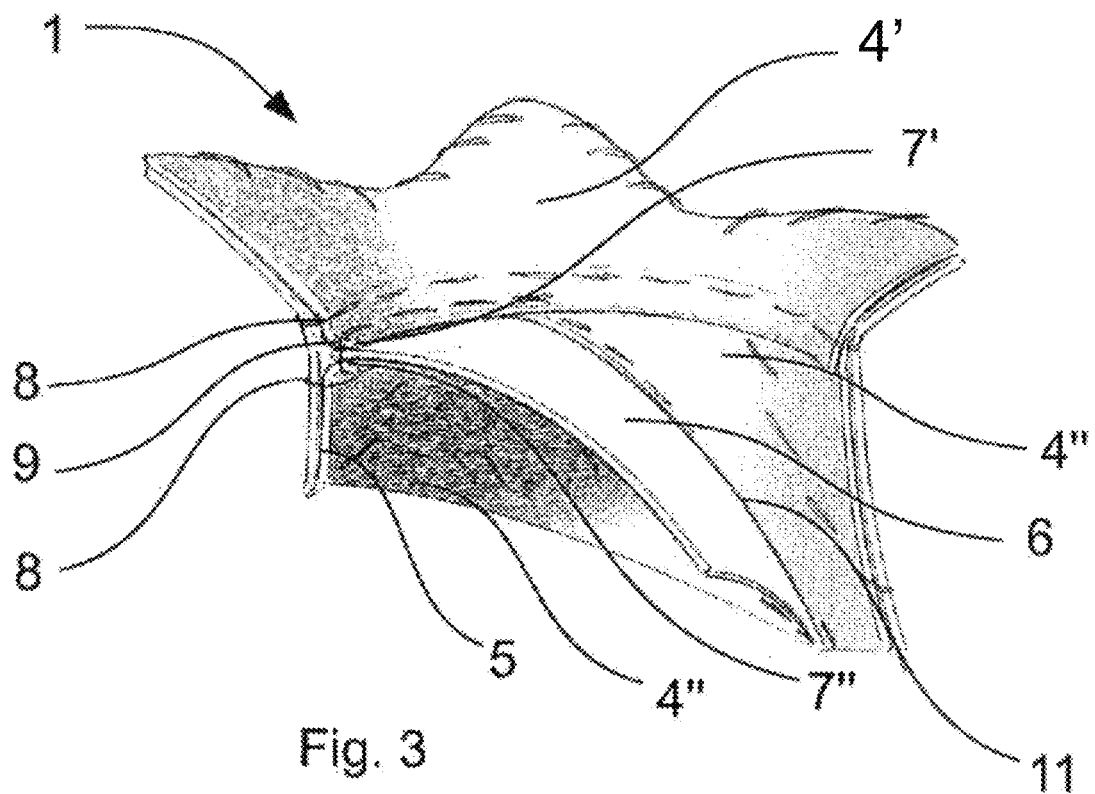

FIG. 3: Another view of a stent-valve according to the invention

Figure 4:
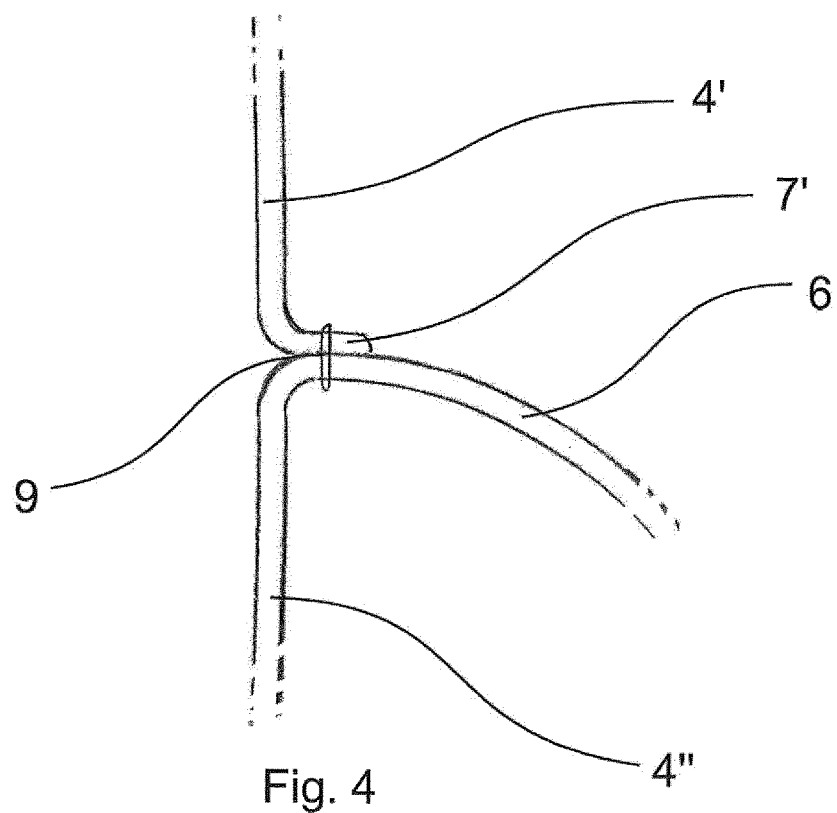

FIG. 4: A longitudinal section through a leaflet and a tissue support according to the invention.

Figure 5:
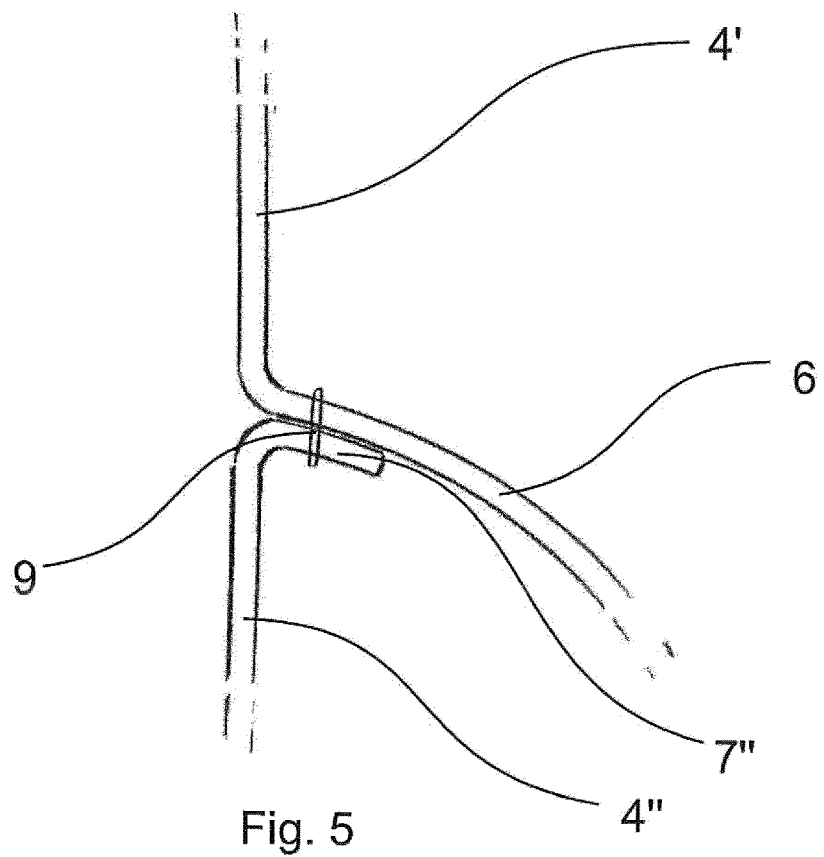

FIG. 5: A longitudinal section through an alternative leaflet and a tissue support according to the invention.

FIG. 6: A view of another embodiment of the invention showing the preparation of a tissue support including a functional leaflet.

FIG. 7: The tissue support and leaflet of FIG. 6 with opposite ends sutures.

Figure 8:
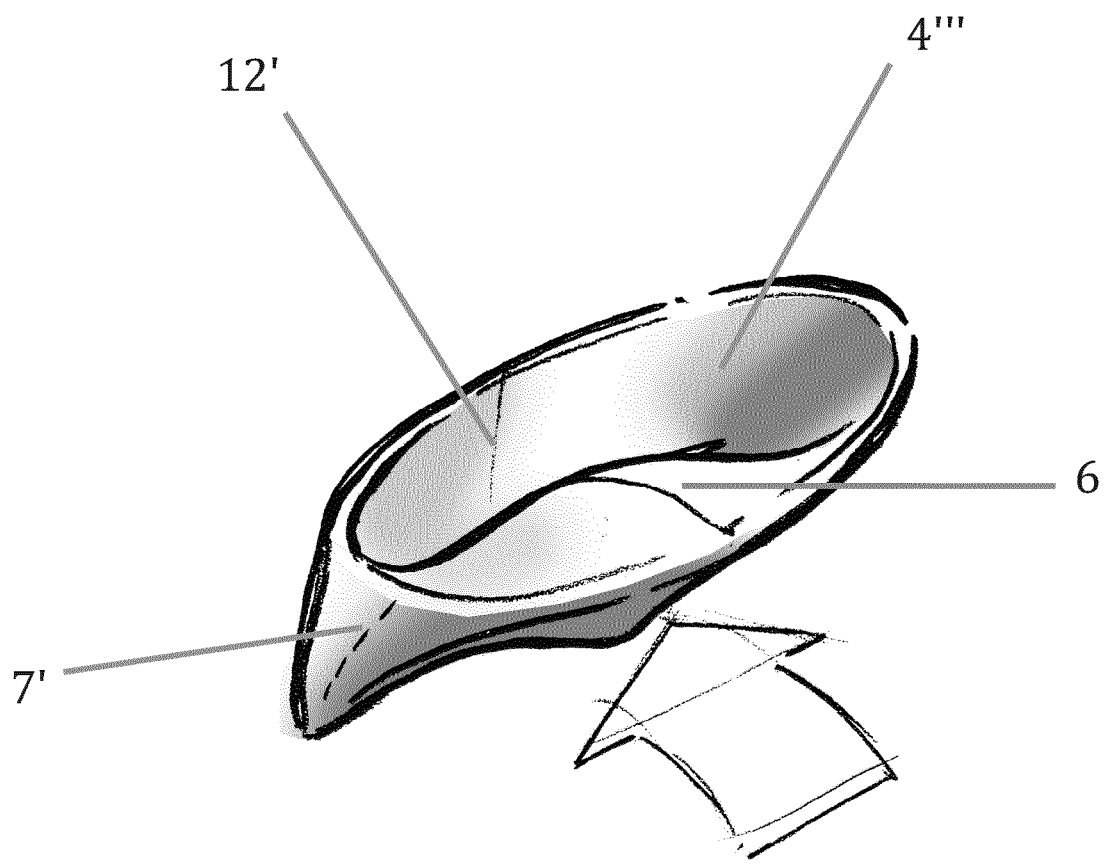

FIG. 8: The embodiment of FIG. 7 viewed from another perspective FIG. 9: The tissue support and leaflet of FIG. 6 with the second tissue support before the attachment.

FIG. 10: A stent-valve made of the tissue supports of FIGS. 6 to 8.

Figure 11:
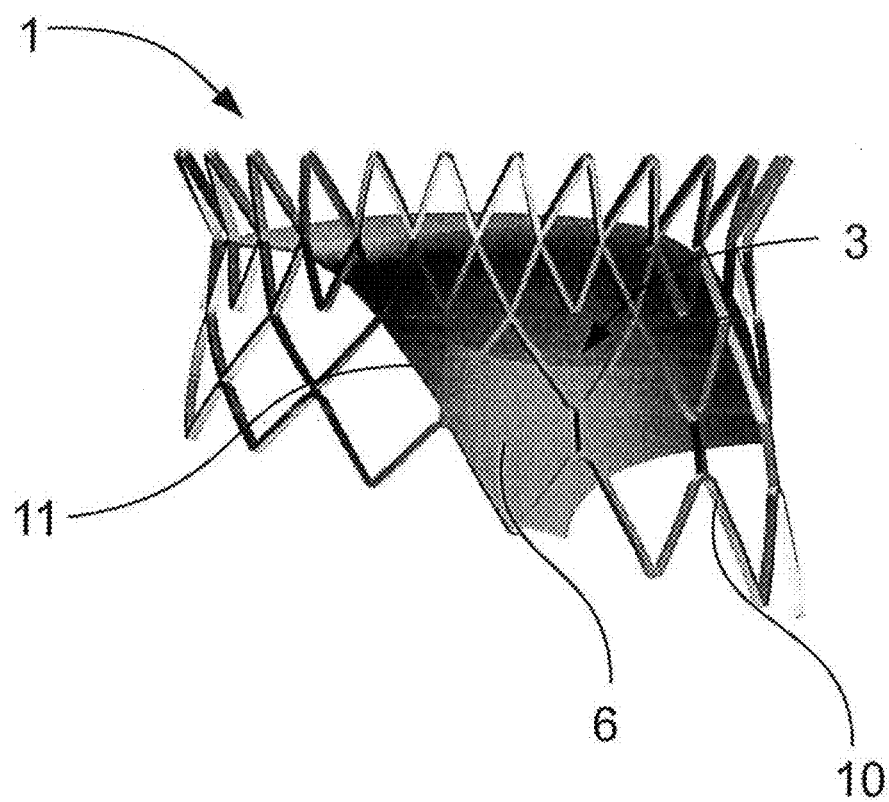

FIG. 11: A view of a stent suitable for the invention.

FIG. 1 shows a longitudinal section through a stent-valve 1. The stent-valve 1 is self expandable and comprises a stent component 2 and a valve component 3. The stent component 2 is substantially made of Nitinol and comprises multiple crossing struts 10. The stent-valve 1 is designed as a mitral valve prosthesis with a mitral valve component 3 comprising a mono leaflet 6. The stent-valve 1 and the leaflet 6 have a D-shape. The D-shape better suits the native conditions of the mitral valve. Two separate support tissues 4', 4" are attached to an inner surface 5 of the stent component 3. Each tissue support 4', 4" comprises an attachment area 7', 7" at its neighbouring end. The attachment areas 7', 7" are extending essentially inwardly from the inner surface 5 towards a centre of the stent-valve 1. The inwardly extending length of the attachment areas 7', 7" is about 2 to 4 mm.

The tissue supports 4', 4" are attached to struts 10 of the stent component 2 with sutures 8. The sutures 8 attaching the tissue supports 4', 4" to the stent component 2 have a distance A (not shown, see FIG. 2) of about 1 to 2 mm. The sutures 8 attaching the tissue support 4', 4" to the stent component 2 nearest to the attachment areas 7', 7" have a distance B to each other which is dependent on the thickness of the pericardial tissue. With a tissue of about 0.3 mm, distance B is about 0.9 to 5 mm, preferably 3 mm. The leaflet 6 is attached to the attachment areas 7', 7" with sutures 9. Stitches of suture 9 have a distance C (not shown, see FIG. 2) of about 1 mm to each other. The inner surface 5 between the sections of the attachment areas 7', 7" attached to the leaflet is not covered with support tissue 4', 4". The distance E between the sutures 8 and the attachment area 7', 7" is about 2 mm. The tissue supports 4', 4" are attached over the inner surface 5 of the stent component 2.

The tissue supports 4', 4" and the leaflet 6 are substantially made of pericardium. The tissue supports 4', 4" are about 0.3 mm thick.

Blood flows through the stent-valve 1 in direction D. The leaflet 6 opens concomitantly with a decreased pressure in the left ventricle during diastole, and the blood flows through the stent-valve 1. After the diastole, the leaflet 6 closes to prevent blood backflow from the left ventricle into the left atrium. During opening of the leaflet 6 (and hence the valve), the attachment areas 7', 7" bend together with the leaflet 6 substantially in direction D and back. The collective bending results in a smooth distribution of the stress acting on the leaflet 6 over the whole area of the leaflet 6 which is in contact with the attachment areas 7', 7". Further, the arrangement provides an elastic chain shock absorption. The two tissue supports 4', 4" and the leaflet 6 cushion any forces during the systo-diastolic cycle, i.e. systo-diastolic opening and closing of the leaflet 6.

FIG. 2 shows a view on the inside of a stent-valve 1. There are two tissue supports 4', 4" attached to the inner surface 5 of the stent component 2. The sutures 8 to attach the tissue supports 4', 4" are arranged along the struts 10 of the stent component 2. The longitudinal cut through the tissue supports 4', 4" is only for illustrative reasons. In use, major parts of the inner surface 5 of the stent-component 2 are covered with tissue supports 4', 4". There might, however, be uncovered portion. Uncovered portions might aid to an unproblematic, easy crimping.

FIG. 3 shows a larger section of the inside of a stent-valve 1. The leaflet 6 is arranged between two tissue supports 4', 4". In neighbouring sections, where no leaflet 6 is attached, the tissue supports 4', 4" are overlapping. The leaflet 6 is attached to the tissue supports 4', 4" along an attachment line 11. By attaching the leaflet 6 to the tissue supports 4', 4" instead of directly to the stent component 2, the orientation of the attachment line 11 is not dependent on the shape of the stent component 2, i.e. the orientation of the struts 10 to which the leaflet 6 might be to. The attachment line 11 can be oriented in an oblique manner with respect to the flow direction D.

FIGS. 4 and 5 show an alternative construction of the tissue supports 4', 4" and the leaflet 6. The leaflet 6 is integrally formed with the tissue support 4" at the outflow end (FIG. 4) or with the tissue support 4' at the inflow en (FIG. 5) of the stent-valve 1. The leaflet 6 is attached to the other support tissue 4', 4" with sutures 9. The stent component 2 is not shown in FIGS. 4 and 5.

FIGS. 6 to 10 show another construction comprising a single piece of tissue, e.g. pericardium, which simultaneously forms a first tissue support 4'" and a functional leaflet 6. A tubular body is initially made from this single piece of tissue, with two opposite end being sutured and wherein the suture 12 is located on the posterior part.

The construction furthermore comprises a second tissue support 4'''' which is attached the functional leaflet 6 on the anterior part.

In this construction the attachment line 7' between the second tissue support 4'''' and the functional leaflet 6 forms an inclined angle.

FIG. 11 shows a stent 1 according to the invention. The stent component 2 is made of multiple crossing struts 10. The valve component 3 is designed as a mono leaflet 6. The tissue supports 4', 4'' are not shown. The leaflet is attached along an attachment line 11 to the tissue supports 4', 4''.

The invention claimed is:

1. A prosthetic heart valve comprising:
   a stent component,
   a first tissue support and a second tissue support, each attached to an inner surface of the stent component, the first tissue support including an attachment area, a section of the attachment area extending essentially inwardly away from the inner surface of the stent component; and
   a single functional leaflet configured to operate as a valve component for opening and closing of the prosthetic valve with a blood flow,
   wherein the single functional leaflet is attached to the first tissue support at the section of the attachment area such that the single functional leaflet is arranged between the attachment area of the first tissue support and an attachment area of the second tissue support, or the single functional leaflet is integrally formed with the first tissue support and attached to the second tissue support at a section of an attachment area of the second tissue support,
   wherein the first tissue support has a tubular shape, the tubular shape made from a single piece of tissue, with two opposite ends of the single piece of tissue having stitches to hold the opposite ends together.

2. The prosthetic valve according to claim 1, wherein the first and the second tissue supports are attached to the inner surface of the stent component and are at least partly covering the inner surface of the stent component.

3. The prosthetic valve according to claim 1, wherein the single functional leaflet is elastic, and the first tissue support includes sutures for attachment to the stent component that are arranged at a distance between 1 mm and 5 mm from the inwardly extending attachment area of the first tissue support.

4. The prosthetic valve according to claim 1, wherein the single functional leaflet is elastic and the first tissue support includes sutures for attachment to the stent component arranged at a distance of about 2 mm from the inwardly extending attachment area of the first tissue support.

5. The prosthetic valve according to claim 1, wherein the single functional leaflet is arranged between the first and second tissue supports, and the first and second tissue supports are separated from each other.

6. The prosthetic valve according to claim 5, wherein the inner surface of the stent component between the attachment areas of the first and second tissue supports is not covered with the first and second tissue supports.

7. The prosthetic valve according to claim 1, wherein the first tissue support is positioned at an inflow end of the prosthetic valve.

8. The prosthetic valve according to claim 1, wherein the single functional leaflet is integrally formed with the first tissue support, the first tissue support is positioned at an outflow end of the prosthetic valve.

9. The prosthetic valve according to claim 1, wherein the single functional leaflet is attached to the attachment area of the first tissue support with sutures.

10. The prosthetic valve according to claim 1, wherein the first and the second tissue supports are attached to the inner surface of the stent component with a first and a second suture, respectively.

11. The prosthetic valve according to claim 10, wherein a distance between the first and the second suture is in a range between 0.9 mm and 5 mm.

12. The prosthetic valve according to claim 10, wherein the first and the second sutures are arranged along struts that form the stent component.

13. The prosthetic valve according to claim 10, wherein the single functional leaflet is attached to the first tissue support and the second tissue support by a third suture, or the single functional leaflet is integrally formed with the first tissue support and attached to the second tissue support by the third suture.

14. The prosthetic valve according to claim 13, wherein the third suture is formed entirely inside the stent component.

15. The prosthetic valve according to claim 1, wherein at least one of the single functional leaflet, the first tissue support, and the second tissue support are substantially made of pericardium.

16. The prosthetic valve according to claim 1, wherein the prosthetic valve is self-expandable.

17. The prosthetic valve according to claim 1, wherein the attachment areas of the first and the second tissue support have a length in a range between 2 mm to 10 mm.

18. The prosthetic valve according to claim 1, wherein the single functional leaflet forms a mitral valve component.

19. The prosthetic valve according to claim 1, wherein the single functional leaflet is elastic, and the second tissue support includes sutures for attachment to the stent component that are arranged at a distance between 1 mm and 5 mm from the attachment area of the second tissue support.

20. The prosthetic valve according to claim 1, wherein the attachment areas are formed partially around a profile of the single functional leaflet when seen in a direction of a blood flow.

21. A prosthetic valve comprising:
    a stent component,
    a first tissue support and a second tissue support, each attached to an inner surface of the stent component, the first tissue support including an attachment area, a section of the attachment area extending essentially inwardly away from the inner surface of the stent component; and
    a single functional leaflet configured to operate as a valve component for opening and closing of the prosthetic valve with a blood flow,
    wherein the single functional leaflet is attached to the first tissue support at the section of the attachment area such that the single functional leaflet is arranged between the attachment area of the first tissue support and an attachment area of the second tissue support, or the single functional leaflet is integrally formed with the first tissue support and attached to the second tissue support at a section of an attachment area of the second tissue support,
    wherein the single functional leaflet is elastic, and the second tissue support includes sutures for attachment to the stent component that are arranged at a distance between 1 mm and 5 mm from the attachment area of the second tissue support.

22. A prosthetic valve comprising:
a stent component,
a first tissue support and a second tissue support, each attached to an inner surface of the stent component, the first tissue support including an attachment area, a section of the attachment area extending essentially inwardly away from the inner surface of the stent component; and
a single functional leaflet configured to operate as a valve component for opening and closing of the prosthetic valve with a blood flow,
wherein the single functional leaflet is attached to the first tissue support at the section of the attachment area such that the single functional leaflet is arranged between the attachment area of the first tissue support and the second tissue support, or the single functional leaflet is integrally formed with the first tissue support and attached to the second tissue support at a section of an attachment area of the second tissue support,
wherein the first and the second tissue supports are attached to the inner surface of the stent component with a first and a second suture, respectively, and
wherein the single functional leaflet is attached to the first tissue support and the second tissue support by a third suture, or the single functional leaflet is integrally formed with the first tissue support and attached to the second tissue support by the third suture.

* * * * *